(12) United States Patent
Baiker

(10) Patent No.: US 6,502,449 B1
(45) Date of Patent: Jan. 7, 2003

(54) TEST STRIP HOLDER FOR SUPPORTING TEST STRIPS MEASURING THE INTENSITY OF SHOT PEENING IN CAVITIES

(75) Inventor: Erwin Baiker, Glattbrugg (CH)

(73) Assignee: Baiker AG, Glattbrugg (CH)

( * ) Notice: Subject to any disclaimer, the term of this patent is extended or adjusted under 35 U.S.C. 154(b) by 65 days.

(21) Appl. No.: 09/640,202

(22) Filed: Aug. 16, 2000

(51) Int. Cl.⁷ .............................. G01L 5/00; G01M 7/00; G01N 3/48
(52) U.S. Cl. .................. 73/11.02; 73/11.01; 73/12; 73/81
(58) Field of Search ............................. 73/11.02, 11.01, 73/12, 432.1, 81, 12.01

(56) References Cited

U.S. PATENT DOCUMENTS 3,695,091 A * 10/1972 Smith ............................. 73/11
5,113,680 A * 5/1992 Matsuura et al. ............... 72/53
5,877,405 A * 3/1999 Champaigne ............... 73/11.02

* cited by examiner

Primary Examiner—Hezron Williams
Assistant Examiner—Katina Wilson
(74) Attorney, Agent, or Firm—Ken C. Decker; James D. Hall

(57) ABSTRACT

A holder for mounting a test strip for measuring the intensity of shot peening in internal cavities includes a receptacle receiving any of multiple inserts configured to form a segment of an internal cavity of a component to be peened. The test strip defines the remainder of the cavity. The shot stream to be measured is introduce into the cavity, after which the test strip is removed and measured in the conventional manner. Accordingly, the intensity of peening in internal cavities may be measured with relative accuracy. By providing multiple inserts, intensity of peening in cavities of varying sizes may be measured by simply changing the insert.

12 Claims, 5 Drawing Sheets

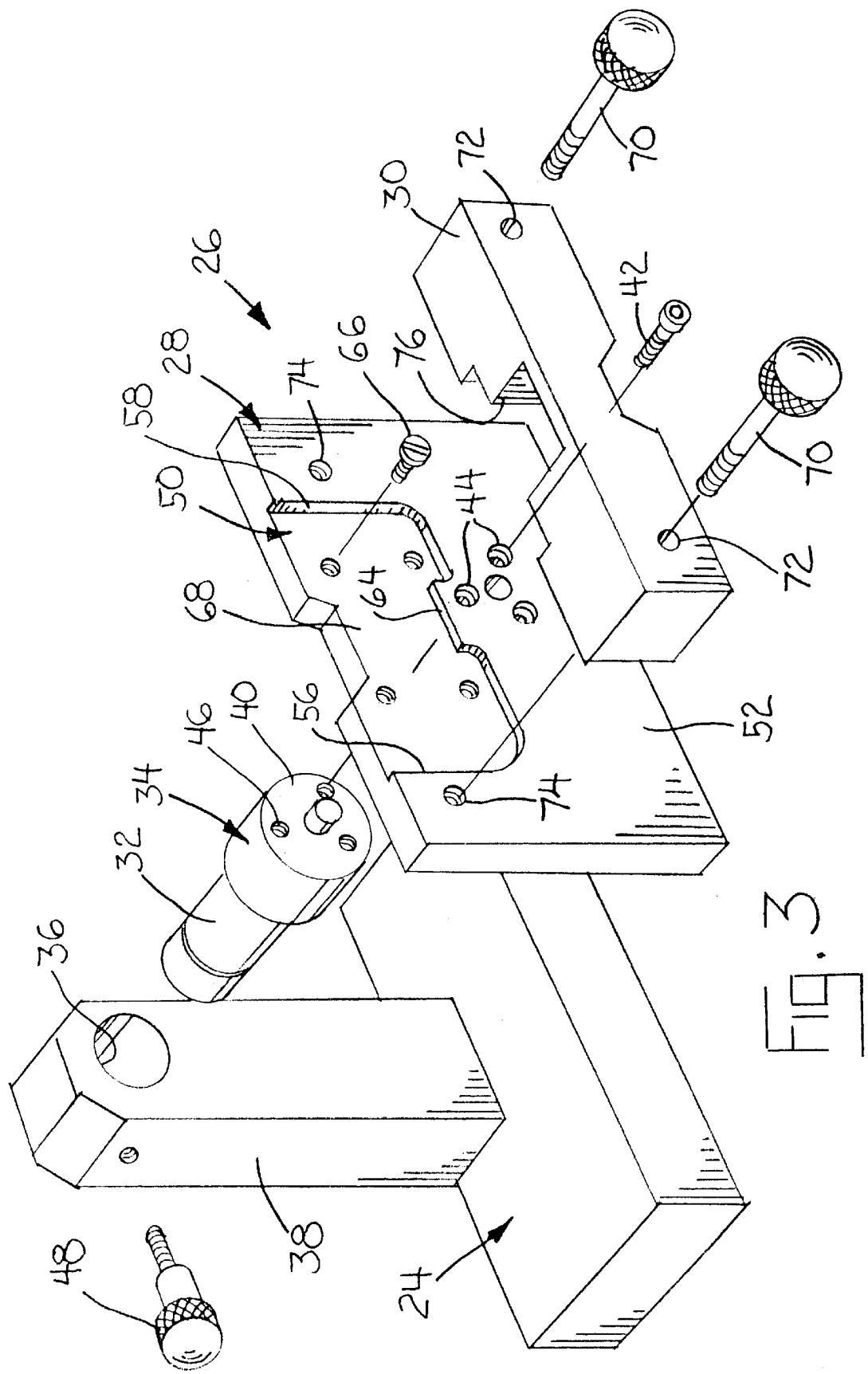

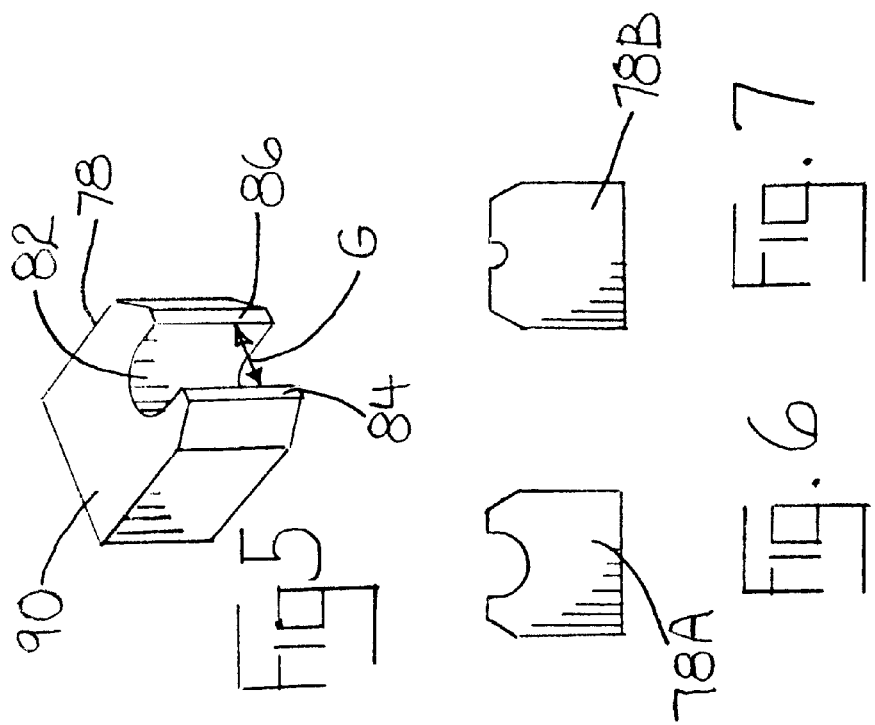
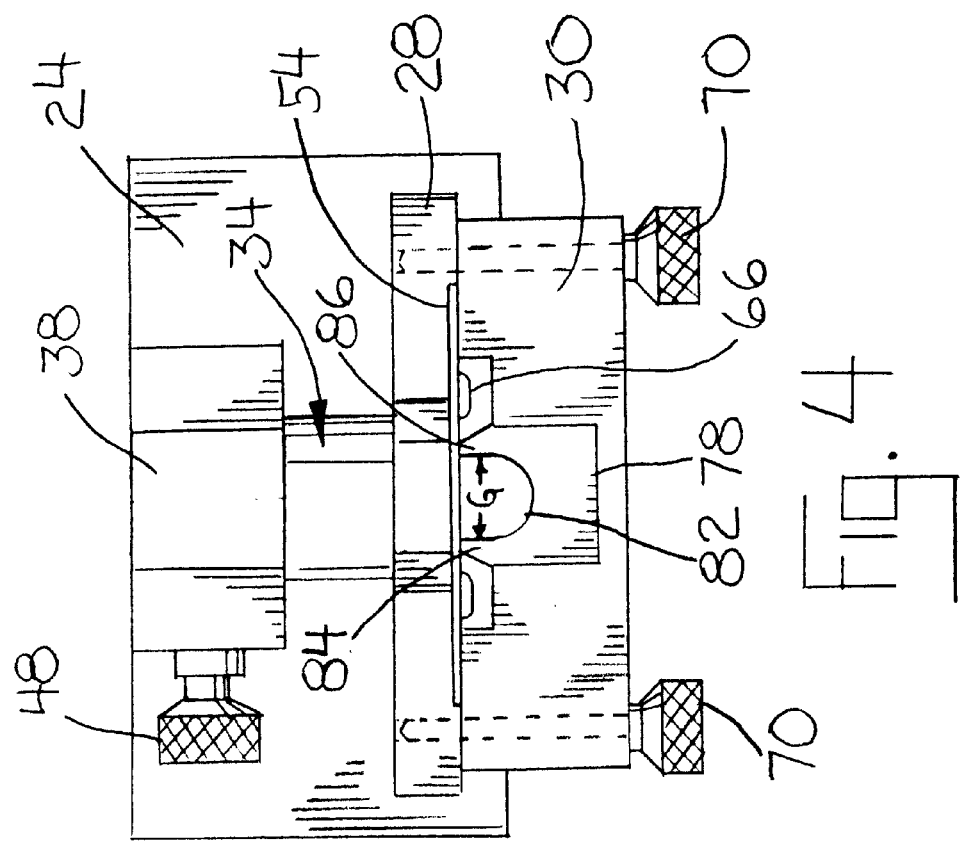

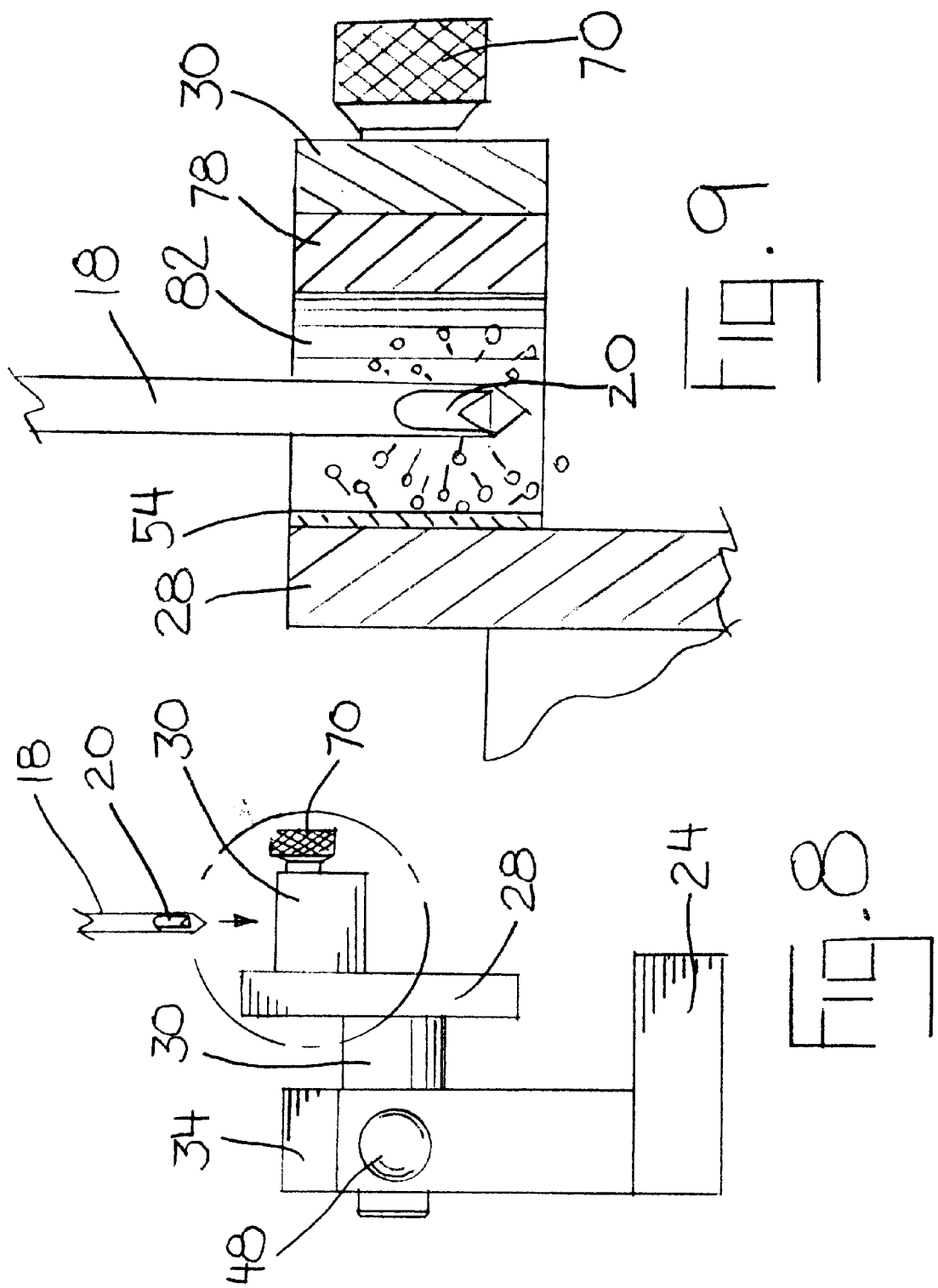

US 6,502,449 B1

TEST STRIP HOLDER FOR SUPPORTING TEST STRIPS MEASURING THE INTENSITY OF SHOT PEENING IN CAVITIES

TECHNICAL FIELD

This invention relates to a holder for supporting a test strip used to measure the intensity of shot peening so that the intensity of shot peening in internal cavities may be controlled.

BACKGROUND OF THE INVENTION

Shot peening is commonly used to work harden critical components. When a component is shot peened, the component is exposed to a stream of shot which impacts upon the component. However, the intensity of shot peening must be carefully controlled, because peening at intensities both above and below a critical range will not harden the component properly. Accordingly, a procedure has been developed to measure the intensity of peening. Commonly, a test strip of known dimensions is mounted on a holder, the peening apparatus is set up in the same manner as it will be used to peen the component, and a stream of shot is directed against the test strip for a predetermined time period. The test strip is then removed from the holder, at which time the test strip relaxes into a natural curvature, the magnitude of which is measured by an appropriate gage, such as the gage disclosed in U.S. Pat. No. 5,297,418. If the measured deflection of the test strip indicates peening intensity within the desired range, peening of the component may be initiated. If the measured deflection is outside of the desired range, the equipment is adjusted, a new test strip is installed in the holder, and the process is repeated.

The foregoing process for measuring the intensity of the peening process works well for surface peening. However, critical components often include internal bores, slots, grooves and similar internal cavities, often having a complex shape, which must be peened. The above intensity measurement process does not yield accurate readings for such internal cavities, since the shot is concentrated in a small volume and ricochets off of the walls of the cavity, thus making measurement of the peening intensity by common methods difficult and inaccurate.

SUMMARY OF THE INVENTION

The present invention provides a relatively accurate measurement of the intensity of shot peening of internal cavities. A conventional test strip is mounted in a holder which includes a receptacle receiving any of multiple inserts configured to form a segment of an internal cavity of a component to be peened. The test strip defines the remainder of the cavity. The shot stream to be measured is introduce into the cavity, after which the test strip is removed and measured in the conventional manner. Accordingly, the intensity of peening in internal cavities may be measured with relative accuracy. By providing multiple inserts, intensity of peening in cavities of varying sizes may be measured by simply changing the insert.

BRIEF DESCRIPTION OF THE DRAWINGS

FIG. 3 is an exploded view in perspective of the test strip holder illustrated in FIG. 2;

FIG. 4 is a top plan view of the test strip holder illustrated in FIGS. 1 and 2;

FIG. 5 is a view in perspective of an insert block used in the test strip holder illustrated in FIGS. 2–4;

FIGS. 6 and 7 are side elevational views of insert blocks similar to those illustrated in FIGS. 6 and 7 but which define cavities of varying sizes;

FIG. 8 is a side elevational view of the test strip holder of FIGS. 1–4; and

FIG. 9 is a fragmentary cross sectional view of the circumscribed portion of FIG. 8

DESCRIPTION OF THE PREFERRED EMBODIMENT

Figure 1:
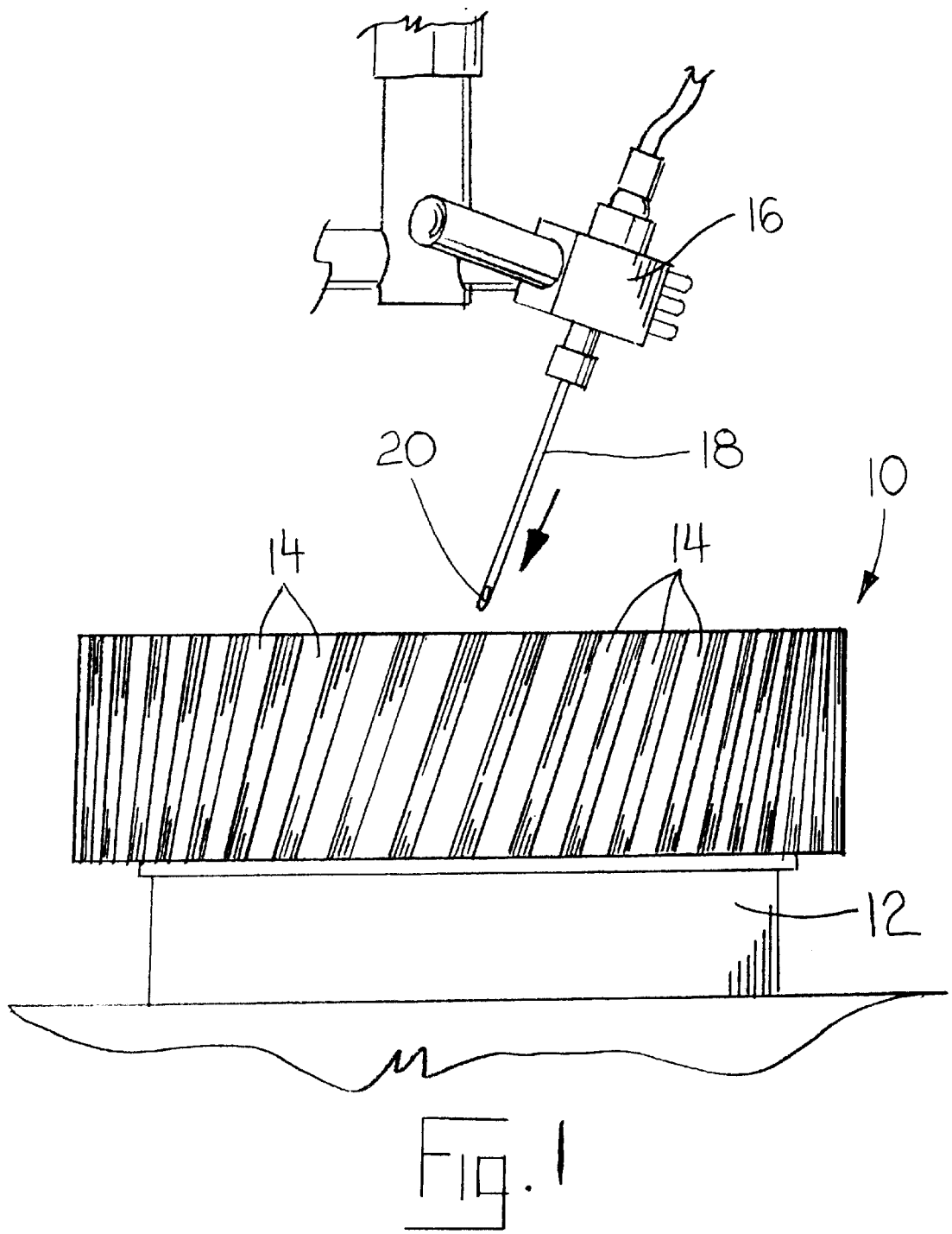
FIG. 1 is a view in perspective of peening equipment and a component having internal cavities which must be peened.

Referring now to FIG. 1 of the drawings, a component undergoing peening is generally indicated by the numeral 10 and is supported on a table 12. The component 10 in this case is the hub of a fan assembly for a turbofan jet engine, but may be any component having bores or grooves requiring internal peening. In this case, the component 10 includes multiple, angulated, circumferentially spaced grooves 14 on the outer circumferential surface of the component 10. The internal surfaces of the grooves 14 are peened by a peening gun 16 of a type well known to those skilled in the art. Shot is dispensed to the peening gun 16 from a suitable source (not shown) and is accelerated by compressed air supplied to the peening gun 16 and delivered through a hollow lance 18, from which it is discharged radially through radial openings 20. The gun 16 is mounted for movement along the axis of the lance 18 and the lance 18 extends at an angle corresponding to the angle of the grooves so that the lance may be moved into and along the grooves 14. Accordingly, internal peening of the grooves 14 may be effected in a manner well known to those skilled in the art.

As discussed above, it is necessary to measure the intensity of the peening in the slots 14, which is commonly effected by peening a test strip of standard dimensions. However, it is also important that peening of the test strip duplicate as nearly as possible the peening of the component 10. Accordingly, since shot will ricochet off of the walls of the groove, it is necessary to accommodate this effect in peening of the test strip, and it is also important that the position of the peening gun 16 not be changed to peen the test strip. The holder 22 permits peening of a test strip while maintaining the setup of the peening gun and also accounts for ricochet of the shot within the slots 14.

Figure 2:
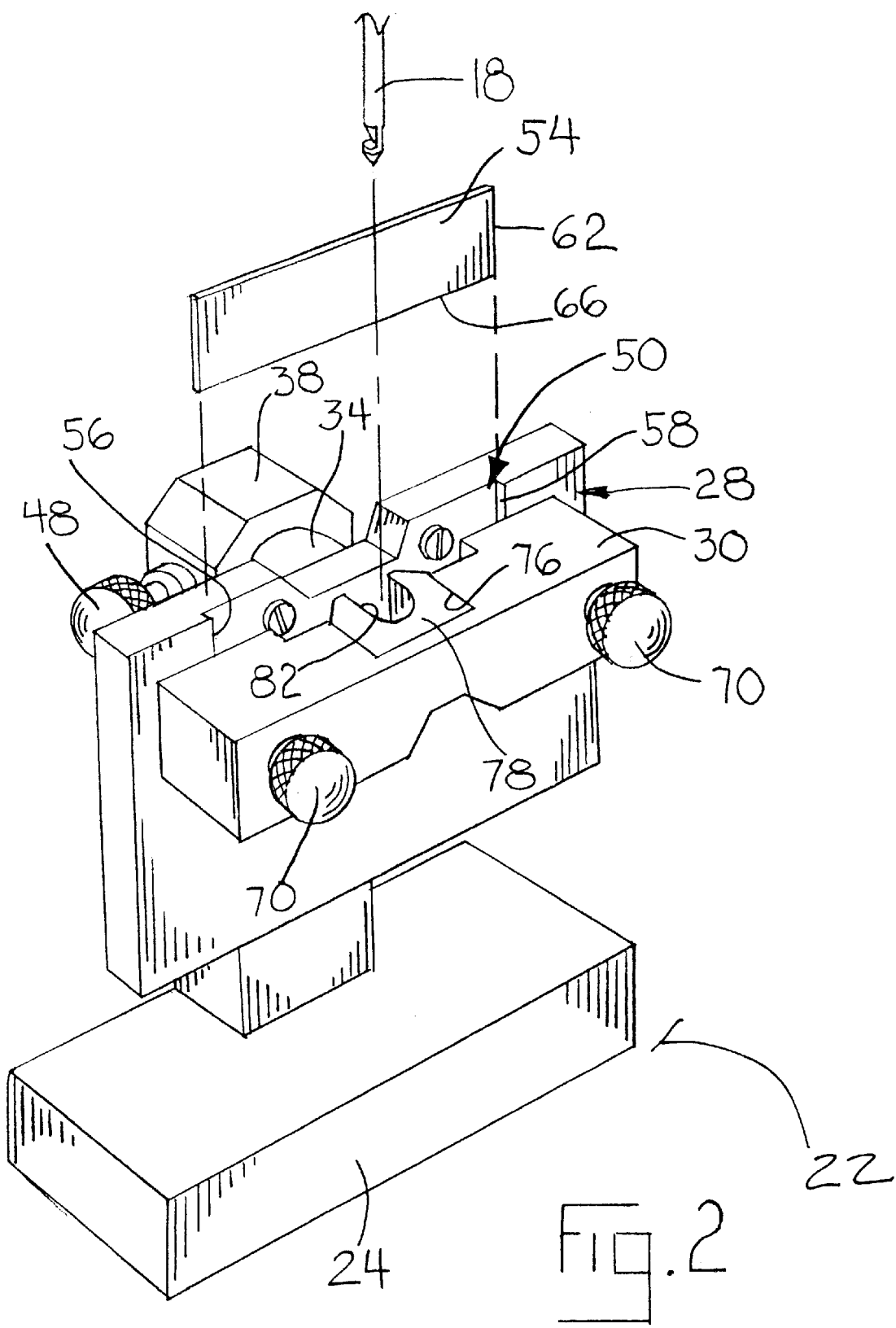
FIG. 2 is a view in perspective of a test strip holder made pursuant to the teachings of the present invention.

Referring now to FIGS. 2 and 3, the holder 22 includes a base 24 and a test strip support 26 which includes a pivotally mounted portion 28 and a removable portion 30. A stepped down section 32 of a cylindrical pivot member 34 is rotatably received in a bore 36 defined within upright portion 38 of the base 24. The pivot member 34 further includes a larger diameter section 40 which is secured to the pivotally mounted portion 28 of support 26 by screws 42, which extend through apertures 44 in portion 28 and are engaged with threaded bores 46 in pivot member 34. Accordingly, the portion 28 is secured for pivotal movement with the pivot member 34 as the pivot member 34 pivots relative to the base 24. A thumbscrew 48 carried by upright portion 38 extends into the bore 36 and may be tightened against the outer circumferential surface of the stepped down section 32 to thereby lock the pivotally mounted portion 28 in a desired angular orientation with respect to the base 24.

A slot 50 is defined in the front face 52 of the portion 28 for locating and supporting a standard peening test strip 54 (FIG. 3) in a testing position. The slot 50 is defined by side edges 56,58 which engage the opposite side edges 60,62 of the strip 54 when the strip 54 is installed in the slot 50, and by a raised portion 64 of the bottom edge of the slot, which engages lower edge 66 of the strip 54. Screws 66 support the strip 54 off of the back face 68 of the slot 50.

The removable portion 30 of support 26 is secured to the pivotally mounted portion 28 by a pair of thumbscrews 70 which extend through apertures 72 in removable portion 30 and are received in threaded apertures 74 in portion 28. The removable portion 30 defines a receptacle or socket 76 which receives any of multiple insert blocks 78 (FIGS. 2,4 and 5). The insert block 78 includes an open sided recess, which is defined by a segment 82 of a circumferentially extending wall. Although the circumferentially extending wall segment 82 is illustrated as curvilinear, the circumferentially extending wall segment 82 may be of any desired shape, including complex shapes which may have linear segments. The segment 82 terminates in opposite edges 84,86 which define a gap G therebetween. As shown in FIGS. 2 and 4, when the insert block 78 is installed in removable portion 30 and the portion 30 is installed on the pivotally mounted portion 28 with the test strip 54 installed in slot 50, the test strip 54 extends across the gap G such that the test strip 54 and wall segment 82 define an internal cavity. The internal cavity has an open end 88 which extends through upper face 90 of the insert block 78. Other insert blocks, such as insert blocks 78a (FIG. 6) and 78b (FIG. 7) may be used to represent cavities having different diameters and configurations, but each of the insert blocks 78, 78a, 78b have the same external dimensions so that each will fit into the receptacle 76.

When the holder 22 is to be used, a test strip is installed in the slot 50 and an appropriate insert block 78 is installed in the receptacle 78. The peening equipment, including the gun 16 and the lance 18, are set up in exactly the same way that they will be used to peen the component 10. Before the component 10 is mounted on table 12, the holder 22 with the test strip and insert block installed therein are placed on the table 12 below the peening gun 16. The thumbscrew 48 is loosened so that the angle of the support 26 may be adjusted relative to the base 24 so that the lance 18 may enter the cavity defined by the wall segment 82 and the test strip 54. The thumbscrew 48 is then tightened to lock the support 26 in position. The lance 18 is lowered into the insert block through the open end 88 and shot is discharged through the lance as the lance is moved along the wall 82 and test strip 54 (as shown in FIGS. 8 and 9), in exactly the same manner that the lance 18 is moved to peen the internal slots 14 of component 10. As illustrated in FIG. 9, shot ricochets off of the wall segment 82, which provides increased peening intensity in addition to that provided by discharge of shot through the lance 18. Accordingly, the intensity of peening of the test strip 54 closely approximates the intensity of peening of the slots 14 of component 10. After peening has been completed, the test strip is removed from the holder 22, by loosening or removing the removable portion 30 of support 26 by operating the thumbscrews 70. After the test strip is removed from the holder, the test strip will curve into a natural deflection, the magnitude of which is a function of the intensity of peening. The magnitude of the deflection is measured by using an appropriate gage, such as the gage disclosed in U.S. Pat. No. 5,297,418, in a manner well known to those skilled in the art.

What is claimed is:

1. Test strip holder for supporting a test strip measuring the intensity of shot peening in cavities, comprising a support defining a cavity, said test strip being mounted on said support and defining a portion of said cavity, said cavity including an opening for receiving accelerated shot whereby shot introduced into said cavity impinges upon said test strip, said cavity being defined by a wall and by said test strip, said cavity being defined by a wall and by said test strip; said wall terminating in an open end of said cavity defining said opening through which said shot is introduced into said cavity; said wall being a segment of a circumferentially extending wall, said segment terminating in a gap defined between ends of said segment, said test strip extending across said gap, whereby the intensity of shot impacting on said test strip is substantially the same as the intensity of shot impacting on said wall, said support including a receptacle receiving a removable insert, said receptacle facing said test strip when the test strip is mounted in said support, said wall terminating in a pair of ends on a face of said insert defining a gap therebetween, said test strip extending cross said gap when the insert is received within said receptacle whereby the test strip cooperates with said wall to define said cavity.

2. Test strip holder as claimed in claim 1 wherein said receptacle receives any of multiple inserts, each of said inserts when installed in the receptacle cooperating with the test strip to defining a cavity of a configuration corresponding to the configuration of the wall defined on the insert.

3. Test strip holder as claimed in claim 1, wherein said support is pivotally mounted on said base, and securing means locking said support in any of multiple angular positions relative to said base.

4. Test strip holder as claimed in claim 1, wherein said wall is curvilinear.

5. Test strip holder as claimed in claim 1, wherein said support includes a pair of sections clamped together by a releasable locking mechanism, one of said sections defining said receptacle, the other section including a support for holding said strip in a test position.

6. Test strip holder as claimed in claim 1, wherein said test strip is mounted on said fixed support facing said cavity when the insert is installed in the receptacle.

7. Test strip holder as claimed in claim 6, wherein said wall terminates in a pair of edges, said edges defining a gap therebetween, said insert extending across said gap, said fixed support including a removable portion releasable secured to another portrion of the fixed support, said removable portion defining said receptacle.

8. Test strip holder for supporting a test strip measuring the intensity of shot peening in cavities, comprising a base, a support mounted on said base, a slot defined in said support for receiving and supporting said test strip in a testing position, said support including a cavity defined by a segment of a circumferentially extending wall defining a gap in said wall and by a segment of said strip extending across said gap, whereby said shot introduced into said cavity impinges upon said wall segment and upon said strip segment, said wall segment being defined on an insert removably received within a receptacle in said fixed support.

9. Test strip as claimed in claim 8, wherein said fixed support includes a pivotally mounted portion pivotally mounted on said base and a removable portion releasably secured to the pivotally mounted portion, said receptacle being defined in the removable portion.

10. Test strip holder for supporting a test strip measuring the intensity of shot peening in cavities, comprising a base, a support mounted on said base, a slot defined in said support for receiving and supporting said test strip in a testing position, said support including a cavity defined by a segment of a circumferentially extending wall defining a gap in said wall and by a segment of said strip extending across said gap, whereby said shot introduced into said cavity impinges upon said wall segment and upon said strip segment, said support is being pivotally mounted on said based whereby the angular orientation of the support may be adjusted with respect to the base.

11. Test strip holder for supporting a test strip measuring the intensity of shot peening in cavities, comprising support means for supporting a test strip in a predetermined position, and cavity defining means cooperating with the support means defining a cavity in which the test strip defines at least a portion of a wall of the cavity, said cavity including means for receiving accelerating shot into said cavity, said cavity defining means including an insert received within a receptacle in said support means, said insert defining a wall defining at least a portion of said cavity.

12. Test strip holder for supporting a test strip measuring the intensity of shot peening in cavities, comprising support means for supporting a test strip in a predetermined position, and cavity defining means cooperating with the support means defining a cavity in which the test strip defines at least a portion of a wall of the cavity, said cavity including means for receiving accelerating shot into said cavity, said support means being pivotally mounted on a base, and releasable latching means permitting the support means to be adjusted with respect to the base.

* * * * *